United States Patent [19]

Fante

[11] 4,307,715

[45] Dec. 29, 1981

[54] AMBULATORY AID

[76] Inventor: Emilie D. Fante, 1045 N. Ferncreek Ave., Orlando, Fla. 32803

[21] Appl. No.: 221,009

[22] Filed: Dec. 29, 1980

[51] Int. Cl.[3] .............................................. A61F 3/00

[52] U.S. Cl. .................................... 128/80 G; 297/5; 272/70.3

[58] Field of Search ..................... 128/80 G; 297/4, 5, 297/6; 272/70.3, 70, 70.4

[56] References Cited

U.S. PATENT DOCUMENTS

| | | | |
|---|---|---|---|
| 2,459,066 | 1/1949 | Duke | 297/5 |
| 3,204,954 | 9/1965 | Scannell | 272/70.4 |
| 3,778,052 | 12/1973 | Andow et al. | 297/5 |
| 4,029,089 | 6/1977 | Molholland | 128/80 G |
| 4,211,426 | 7/1980 | Motloch | 272/70.3 |

*Primary Examiner*—John D. Yasko

*Attorney, Agent, or Firm*—Duckworth, Allen, Dyer & Pettis

[57] ABSTRACT

An ambulatory aid for use with conventional, physical therapy walker railings of the type found in most hospitals includes a horizontal rod extending from a patient brace to each of the walker railings, with means for holding the patient to the brace and the ends of the rod to the railings. The aid has wheels and stabilizers coupled with the brace and rod to prevent the patient from falling forward or backward while moving between the walker railings, and is provided with a handle attached to the rod and brace for further patient support.

15 Claims, 2 Drawing Figures

AMBULATORY AID

BACKGROUND OF THE INVENTION

1. Field of the Invention

The present invention relates generally to physical therapy devices and methods, and particularly relates to devices for assisting a patient in walking between parallel, approximately waist-high physical therapy walker railings of the type found in hospitals, nursing homes and other health care facilities.

2. Description of the Prior Art

In hospitals, health care centers, nursing homes and other facilities, various devices have been used to assist patients in regaining mobility, strengthening muscles and generally assisting a person walking or attempting to walk.

Many persons who receive physical therapy in such institutions to assist them in walking are often taught to use walker railings which are approximately waist-high and parallel. Persons using such bars are often assisted by physical therapists who encourage use of such railings to walk without the assistance. However, occasionally patients attempting to walk without any assistance other than the railings have difficulty because of their weakness and infirmity.

Prior patents pertaining to ambulatory aids include the following:

(1) U.S. Pat. No. 1,307,058 - McGrath
(2) U.S. Pat No. 1,394,224 - Scott
(3) U.S. Pat No. 2,210,269 - Taylor
(4) U.S. Pat. No. 2,812,010 - Abdallah
(5) U.S. Pat. No. 3,165,314 - Clearman et al.
(6) U.S. Pat. No. 3,295,517 - Stevens
(7) U.S. Pat. No. 3,557,782 - Wafer
(8) U.S. Pat. No. 3,827,429 - Heikes
(9) U.S. Pat. No. 3,986,502 - Gilson
(10) U.S. Pat. No. 4,188,966 - Palmer et al.

In U.S. Pat. No. 1,307,058, McGrath discloses a four-wheeled walking chair with two crutches extending upward from the sides of the chair. A person stands in the center of that chair between the crutches and is able to rest or sit on a bicycle-like seat located above the four wheels and between the crutches.

In U.S. Pat. No. 1,394,224, Scott discloses a rolling crutch similar to McGrath's walking chair, and includes two horizontal, parallel bars attached to its sides at about shoulder height.

In U.S. Pat. No. 2,210,269, Taylor discloses a wheeled arrangement with straps and braces for attachment to the patient's legs.

In U.S. Pat. No. 2,812,010, Abdallah discloses two parallel rails with a body trunk harness attached to an overhead railing. Support is provided from above the patient, who is suspended from above while walking between the parallel bars.

In U.S. Pat. No. 3,165,314, Clearman et al. disclose a motorized, three-wheeled invalid walker and ambulatory aid.

In U.S. Pat. No. 3,295,517, Stevens discloses leg boosters to relieve body fatigue. The arrangement disclosed attaches to the human body as a full body harness.

In U.S. Pat. No. 3,557,782, Wafer discloses a brace apparatus attached to a patient's legs beneath the knees, to assist in maintaining equilibrium by extending the surface area of contact made between the lower extremities and the floor.

In U.S. Pat. No. 3,827,429, Heikes discloses an ambulatory orthopedic traction apparatus having a vertical bow attached to a waist-encircling belt to permit support from above of the neck or other parts of the upper torso.

In U.S. Pat. No. 3,986,502, Gilson discloses an ambulation assistance device attachable to the patient's legs.

In U.S. Pat. No. 4,188,966, Palmer et al. disclose a walking support device comprising a four-wheeled unit which attaches to the patient's trunk and rolls on the floor with the patient.

SUMMARY OF THE INVENTION

The general purpose of the present invention is to provide assistance to a person walking or attempting to ambulate. The invention provides support and restraint for the person using it and assists in developing the ambulatory strength of the person. The ambulatory aid of the present invention utilizes conventional parallel walker railings in assisting a person to ambulate without falling forward or backward and without having to hang from a support above the patient's body.

The present invention contemplates an ambulatory aid particularly adapted for use with the conventional, approximately waist-high physical therapy walker railings of the type found in hospitals, nursing homes and the like for assisting a patient in ambulating in a forward direction between the railings, the aid comprising a patient brace and means for holding the patient against the brace. Also included is a rod fixed with, and extending laterally from each edge of the brace, and means at the outer extremity of each rod for making low friction contact with the railings, to thereby permit a patient in the brace to ambulate in the forward direction without holding on the railings.

In a preferred embodiment, the aid is also provided with a handle extending upwardly from the lower extremity of the brace, and low friction floor engaging and stabilizing means coupled with the brace for permitting movement along the forward direction and for preventing a patient in the brace from falling forward or backward while moving between the railings in the forward direction.

DETAILED DESCRIPTION OF THE PREFERRED EMBODIMENT

Figure 1:
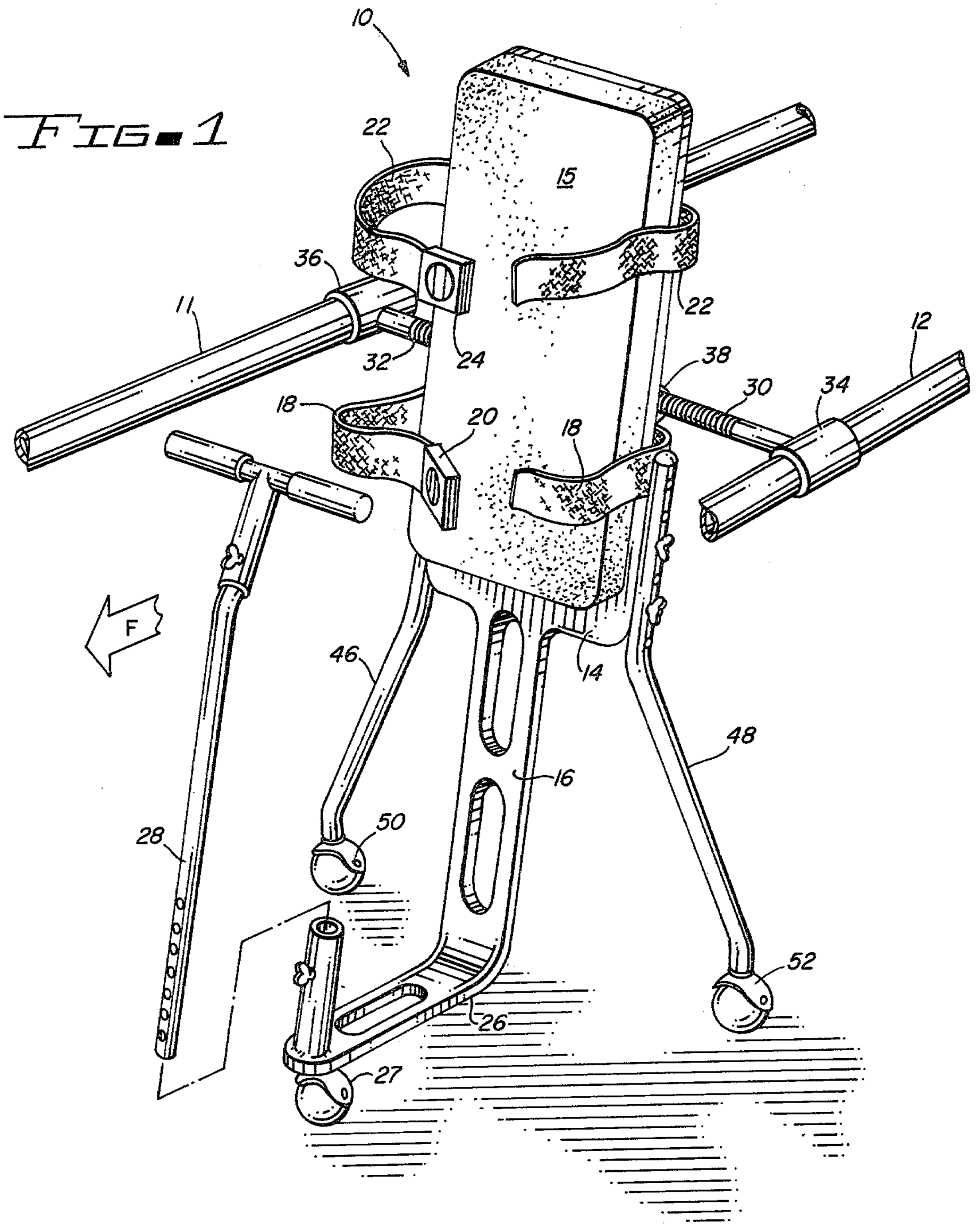
FIG. 1 is a perspective view illustrating the ambulatory aid of the present invention.

A detailed description of the preferred embodiment of the present invention will now be described with reference to FIGS. 1 and 2.

The ambulatory aid of the present invention, referred to generally with the reference numeral 10, is adapted for use with conventional, approximately waist-high physical therapy walker railings of the type found in hospitals, nursing homes and the like for assisting a patient in developing walking muscles in the leg after a long illness.

The aid 10 includes a brace comprising a plate 14 having a padded forward surface 15 for patient comfort, the upper portion of the plate 14 having a dimension sufficiently wide to extend across the back of a typical patient, and a lower plate extension 16 which is substantially thinner than the upper portion to extend downwardly toward the floor. The aid 10 includes lower-waist straps 18 secured at the peripheral edge of the plate 14, and adapted to be coupled together by a buckle 20 in front of the patient; and a second pair of straps 22 above the first pair of straps 18, and adapted to encircle the patient's chest and be joined at the front thereof by a buckle 24.

The aid 10 is further provided with a handle support base 26 extending forwardly from the lower extremity of the plate extension 16, to support a handle 28 extending upward between the railings 11, 12. A roller 27, such as a conventional caster, is fixed to the underside of the support base 26.

Figure 2:
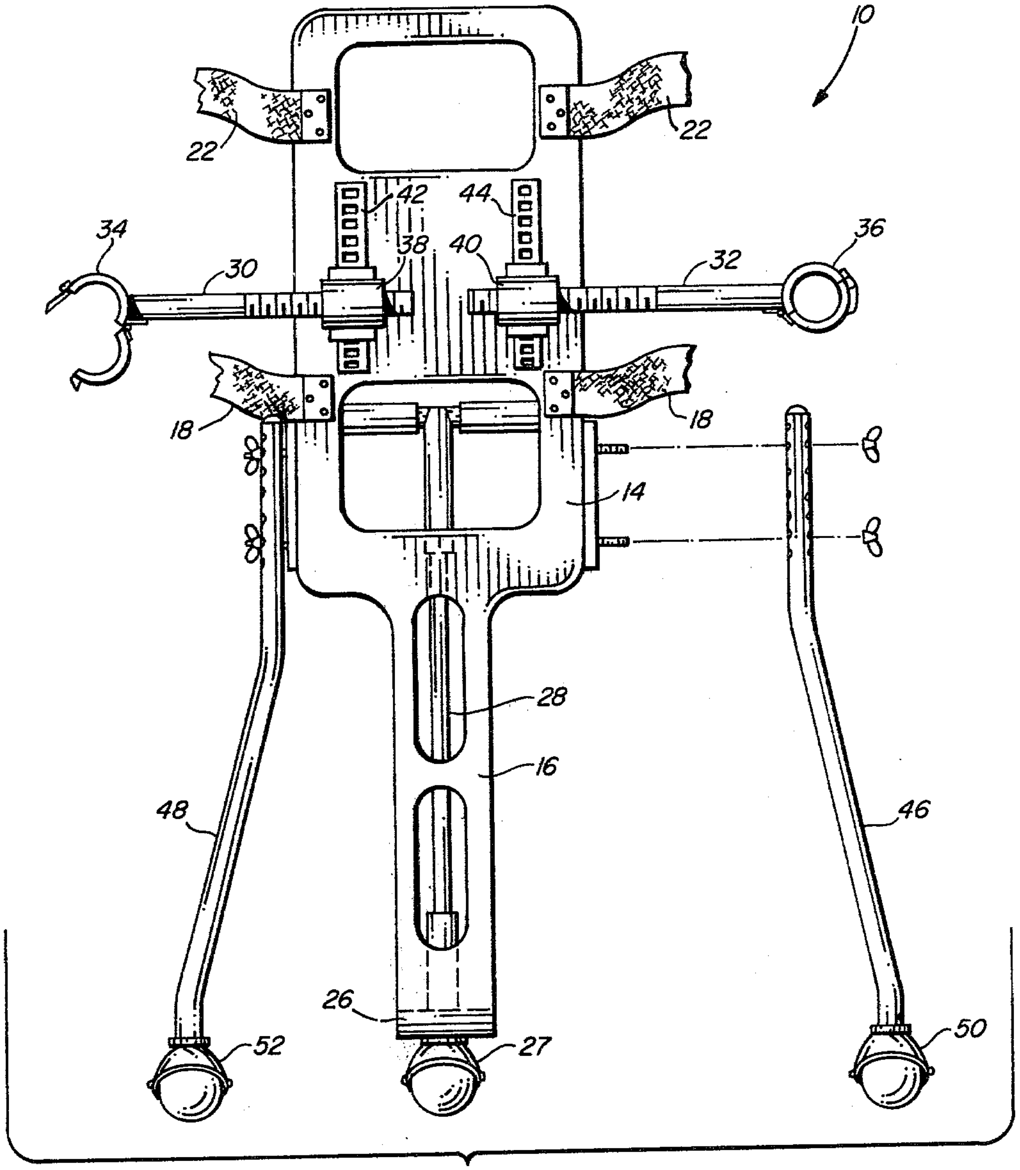
FIG. 2 is a rear view of the ambulatory aid of FIG. 1, illustrating certain details.

Noting particularly FIG. 2, the aid 10 includes a pair of threaded rods 30, 32, each extending laterally from each edge of the brace and toward a respective one of the railings 11, 12. A bearing member 34, 36 is fixed to the outer extremity of each threaded rod 30, 32 and is adapted to encircle a corresponding one of the walker railings 11, 12. (Note FIG. 1.) Conventionally, each bearing member is adapted to have its lower half hinged so as to permit its removal from the corresponding one of the walker railings 11, 12. Such arrangements are conventional, and do not constitute a part of this invention. Further, the bearing members 34, 36 may include internal ball or needle bearings to insure low friction contact between the respective bearing member 34, 36, and the corresponding walker railing 11, 12.

Each threaded rod 30, 32 is engaged with a corresponding threaded sleeve 38, 40, each sleeve in turn being mounted to a bracket 42, 44 attached to the back side of the plate 14. This arrangement permits adjustment of the lateral dimension between each edge of the plate 14 and the corresponding bearing member 34, 36, and likewise permits vertical adjustment of each threaded rod 30, 32.

The aid 10 further includes a pair of support struts 46, 48, each extending rearwardly and downwardly from an opposite edge of the plate 14, and each including a corresponding roller 50, 52 (conventional casters) for permitting low friction engagement with the floor and for stabilizing the aid to reduce the likelihood that the patient will fall forward or backward while moving between the railings in the forward direction.

The manner of use of the aid 10 will now be described with reference to FIG. 1.

Initially, the aid 10 is strapped to the patient, and the patient is then positioned between the walker railings 11, 12. Appropriate adjustments may be made to the vertical height and lateral dimensions of the threaded rods 30, 32 to engage the respective bearing members 34, 36 to a corresponding one of the walker railings 11, 12. When properly positioned, the casters 27, 50 and 52 are in engagement with the floor, while the patient's feet rest on the floor with the knees at most slightly bent. The patient may then grip the handle 28, and move slowly in the forward direction, as indicated by the arrow and the letter "F" in FIG. 1. The patient may then engage in the physical therapy of walking between the walker railings 11, 12 without the assistance of a physical therapist or the like.

It will be understood by those skilled in the art that various modifications in the arrangement shown in FIGS. 1 and 2 may be made without departing from the spirit and scope of the present invention. For example, it may be possible to omit the handle and base assembly 26, 28 as well as the rearward stabilizing assembly including the struts 46, 48 and the rollers 50, 52 to obtain another embodiment of the present invention that permits a patient to be supported between conventional walker railings while walking for physical therapy. Of course, the rearward stabilization assembly and the handle assembly serve useful purposes under certain circumstances.

I claim:

1. An ambulatory aid for use with conventional, approximately waist-high physical therapy walker railings of the type found in hospitals, nursing homes and the like for assisting a patient in ambulating in a forward direction between said railings, said aid comprising:

(a) a patient brace;

(b) means for holding a patient against said brace;

(c) a rod fixed with, and extending laterally from each edge of said brace; and (d) means at the outer extremity of each said rod for making low friction contact with said railings, to thereby permit a patient in said brace to ambulate in said forward direction without holding on to said railings.

2. The ambulatory aid recited in claim 1, further comprising low friction floor engaging and stabilizing means coupled with said brace for permitting movement along said forward direction and for preventing a patient in said brace from falling forward or backward while ambulating between said railings in said forward direction.

3. The ambulatory aid recited in claim 2 further comprising a handle fixed with said brace and extending in said forward direction so as to permit a patient to grip said handle while held in said brace.

4. The ambulatory aid recited in claim 3 wherein said brace comprises a flat plate adapted to extend vertically between said railings, said plate having padding along a front side thereof.

5. The ambulatory aid recited in claim 4 wherein each said rod is adjustably fixed with the back side of said plate to permit vertical adjustment thereof.

6. The ambulatory aid recited in claim 5 further comprising means for adjusting the lateral dimensions of each said rod away from said plate.

7. The ambulatory aid recited in claim 4 wherein said patient holding means comprises a pair of straps attached along opposing edges for encircling the patient, and a buckle for adjustably coupling said straps together.

8. The ambulatory aid recited in claim 4 wherein said low friction contact means at the end of each said rod comprises a bearing member encircling the corresponding one of said railings.

9. The ambulatory aid recited in claim 8 wherein said low friction floor engaging means comprises:

(a) a pair of support struts, each strut extending rearwardly and downwardly from said plate; and (b) a roller coupled to the extremity of each said strut for making said low friction engagement with the floor.

10. The ambulatory aid recited in claim 9 further comprising:

(a) a handle support base extending laterally from the lower extremity of said plate and in said forward direction with said handle extending upwardly from said base; and (b) a roller coupled under said base and adapted for low friction engagement with the floor.

11. An ambulatory aid for use with conventional, approximately waist-high physical therapy walker railings of the type found in hospitals, nursing homes and the like for assisting a patient in ambulating in a forward direction between said railings, said aid comprising:

(a) a flat plate adapted to extend vertically between said railings, said plate having padding along a front side thereof;

(b) means including a pair of straps attached along opposing edges of said plate for encircling the patient and a buckle for adjustably coupling said straps together, for holding a patient against said brace;

(c) a rod extending laterally from each edge of said plates;

(d) a bearing member at the end of each rod for making low friction contact with the corresponding one of said railings; and (e) means for adjusting the lateral dimension between each edge of said plate and the corresponding bearing member.

12. The ambulatory aid recited in claim 11 further comprising low friction floor engaging and stabilizing means coupled with said brace for permitting movement along said forward direction and for preventing a patient in said brace from falling forward or backward while moving in between said railings in said forward direction.

13. The ambulatory aid recited in claim 12 wherein said low friction floor engaging means comprises:

(a) a pair of support struts, each strut extending rearwardly and downwardly from said plate; and (b) a roller coupled to the extremity of each said strut for making said low friction engagement with the floor.

14. The ambulatory aid recited in claim 11 further comprising a handle fixed with said plate and extending in said forward direction so as to permit a patient to grip said handle while held in said plate.

15. The ambulatory aid recited in claim 14 further comprising:

(a) a handle support base extending laterally from the lower extremity of said plate and in said forward direction, with said handle extending upwardly from said base; and (b) a roller coupled under said base and adapted for low friction engagement with the floor.

* * * * *